(12) United States Patent
Nagashimada et al.

(10) Patent No.: US 6,493,069 B1
(45) Date of Patent: Dec. 10, 2002

(54) METHOD AND INSTRUMENT FOR MEASURING BLOOD SUGAR LEVEL

(75) Inventors: Masaru Nagashimada, Yamanashi-ken (JP); Syozo Ohyu, Yamanashi-ken (JP)

(73) Assignee: Terumo Kabushiki Kaisha, Shibuya-Ku (JP)

( * ) Notice: Subject to any disclaimer, the term of this patent is extended or adjusted under 35 U.S.C. 154(b) by 146 days.

(21) Appl. No.: 09/679,280

(22) Filed: Oct. 6, 2000

Related U.S. Application Data

(63) Continuation-in-part of application No. 09/358,430, filed on Jul. 22, 1999.

(30) Foreign Application Priority Data

Jul. 24, 1998 (JP) .......................................... 10-209997

(51) Int. Cl.⁷ .......................... G01N 33/48; G01N 21/00
(52) U.S. Cl. .......................................... 356/39; 422/56
(58) Field of Search ..................... 356/39–42, 445–448, 356/73; 364/413.07; 436/164–172; 422/55, 56, 58, 82.05, 82.09

(56) References Cited

U.S. PATENT DOCUMENTS

| | | | |
|---|---|---|---|
| 5,231,576 A | * 7/1993 | Suzuki et al. .......... 364/413.09 |
| 5,304,468 A | 4/1994 | Phillips et al. ................. 435/14 |
| 5,316,727 A | * 5/1994 | Suzuki et al. ............... 422/68.1 |
| 5,397,537 A | * 3/1995 | Kanda et al. .................. 422/56 |
| 5,597,532 A | 1/1997 | Connolly ...................... 422/58 |
| 5,885,839 A | * 3/1999 | Lingane et al. ................ 436/34 |
| 5,889,585 A | * 3/1999 | Markart ........................ 356/39 |

FOREIGN PATENT DOCUMENTS

| EP | 0 199 484 | 10/1986 |
|---|---|---|
| WO | 88/00812 | 2/1988 |

* cited by examiner

Primary Examiner—Michael P. Stafira
(74) Attorney, Agent, or Firm—Burns, Doane, Swecker & Mathis, LLP (57) ABSTRACT

A blood sugar measuring instrument for measuring the blood sugar level of blood on the basis of change in the color of the reagent having reacted with the blood. The instrument irradiates light onto a specimen to which blood is applied, detects the intensity of the reflected light with a photo detector, determines absorbency from the specimen every one second after the specimen has started coloring by the applied blood, and calculates the blood sugar level of the blood applied to the specimen on the basis of the absorbency when change in the absorbency has become 2% or less.

20 Claims, 13 Drawing Sheets

METHOD AND INSTRUMENT FOR MEASURING BLOOD SUGAR LEVEL

This application is a continuation-in-part of application Ser. No. 09/358,430 filed on Jul. 22, 1999, the entire content of which is incorporated herein.

BACKGROUND OF THE INVENTION

The present invention relates to a method of measuring blood sugar level for measuring the glucose concentration in blood, and an instrument therefor.

Heretofore, there has been known a blood sugar measuring instrument for measuring the blood sugar level of the blood of a subject by applying blood collected from a finger of the subject to a reagent pad, and by detecting change in color of the reagent pad. In such a blood sugar measuring instrument, light is radiated to the reagent pad, the intensity of reflected light from the reagent pad is measured, and the blood sugar level of the blood applied to the reagent pad is determined.

Change in color of such a reagent pad depends upon the length of time elapsed from the time when the blood was applied to the reagent pad. In the normal practice, therefore, the length of time until the reagent of the reagent pad reacts with glucose in blood is empirically determined, and after the empirically determined time (predetermined time) has elapsed after a subject or a user had instructed the start of measurement, the above-described intensity of reflected light is detected, and the blood sugar level is determined.

In such a method, however, there is dispersion in the length of time after allowing the subject to apply blood to the reagent pad until depressing the switch to instruct the start of measurement. Therefore, even if measurement is started after the predetermined time has elapsed after the start of measurement had been instructed, the result of measurement may include error. Also, if measurement was started after the predetermined time had elapsed considering the delay in time after applying blood to the reagent pad until instructing the start of measurement without using the above-described switch, there was a problem in which the subject or the user always had to wait for longer time resulting in increase in time required for measurement.

SUMMARY OF THE INVENTION

An object of the present invention is to provide a method and an instrument for measuring blood sugar level which can measure blood sugar level accurately by automatically determining appropriate timing for measurement, taking the above-described conventional methods and instruments into consideration.

Another object of the present invention is to provide a method and an instrument for measuring blood sugar level which can determine timing for starting measurement automatically corresponding to change in the color of the reagent pad.

Still another object of the present invention is to provide a method and an instrument for measuring blood sugar level which can plainly inform the subject or the user of the process state of blood sugar level measurement.

In order to attain the above objects, the instrument for measuring blood sugar level of the present invention has the following processes:

A blood sugar measuring instrument for measuring the blood sugar level of blood impregnated in a reagent layer of a specimen includes an irradiation mechanism for irradiating light towards the reagent layer, a reflected light detecting device for detecting the intensity of the light reflected from the reagent layer, a calculator for calculating an average value of the intensity per each second, based on the intensity detected by the reflected light detecting device for plural seconds, and a determination device for determining whether or not a change in average values of the intensity calculated by the calculator has become a first predetermined value or less. A blood sugar calculator then calculates the blood sugar level of the blood on the basis of the average value when the determination device determines that the change has become the first predetermined value or less.

According to another aspect of the invention, a method for measuring the blood sugar level of blood impregnated to a reagent layer of a specimen involves directing light toward the reagent, detecting the intensity of light reflected from the reagent, calculating an average value of the intensity each second based on the intensities detected over plural seconds, determining a change in the average value, determining whether the change in the average value has reached a first predetermined value or less, and calculating the blood sugar level of the blood based on the average value when the change in the average value has reached the first predetermined value or less.

Other features and advantages of the present invention will be apparent from the following descriptions taken in conjunction with the accompanying drawings, in which like reference characters designate the same or similar parts throughout the figures thereof.

BRIEF DESCRIPTION OF THE DRAWING FIGURES

The accompanying drawings, which are -incorporated in and constitute a part of the specification, illustrate embodiments of the invention and, together with the descriptions, serve to explain the principle of the invention.

DESCRIPTION OF THE PREFERRED EMBODIMENTS

The preferred embodiments of the present invention will be described in detail below referring to attached drawings.

Figure 1:
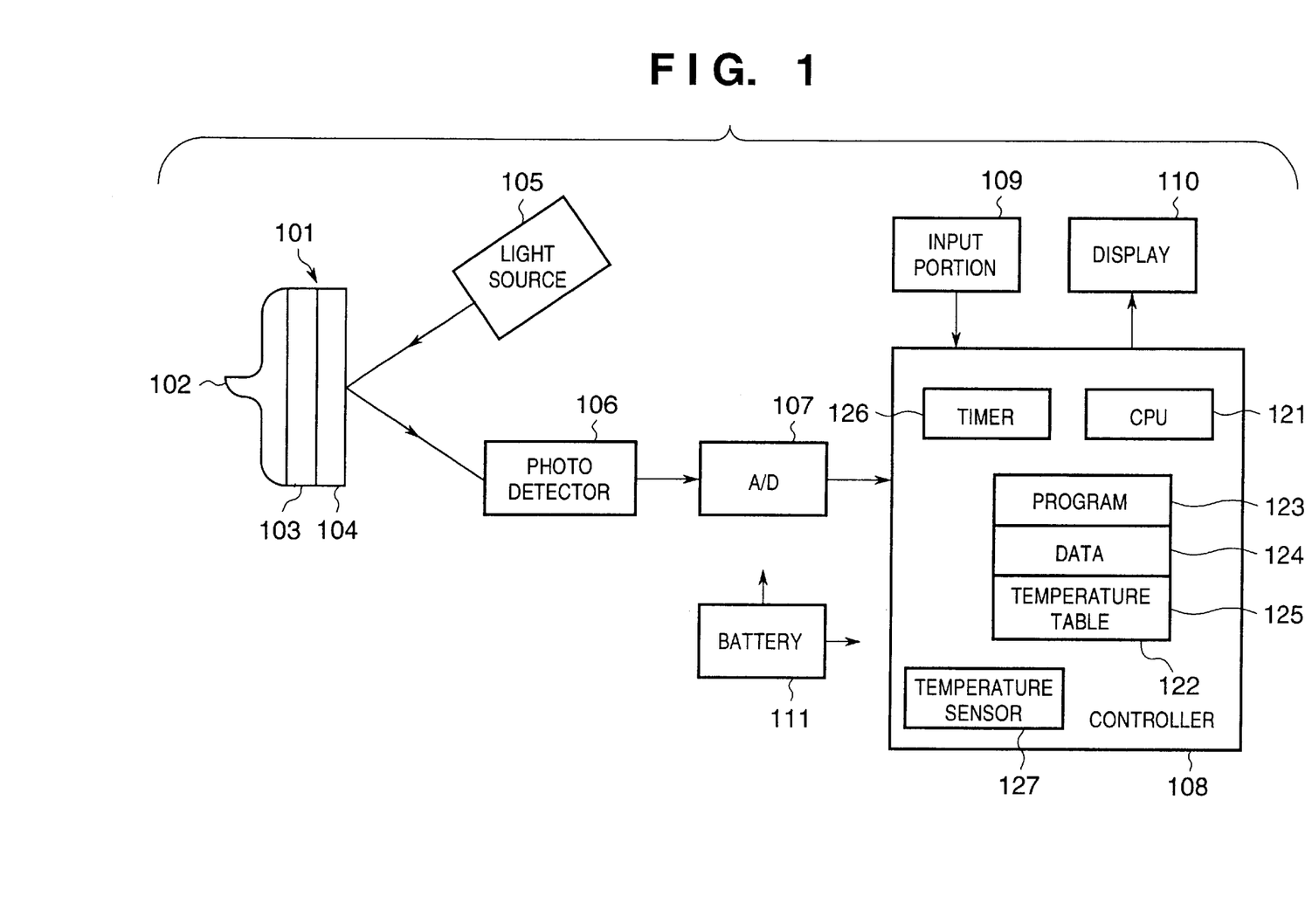
FIG. 1 is a block diagram showing the constitution of a blood sugar measuring instrument of an embodiment of the present invention.
Figure 2:
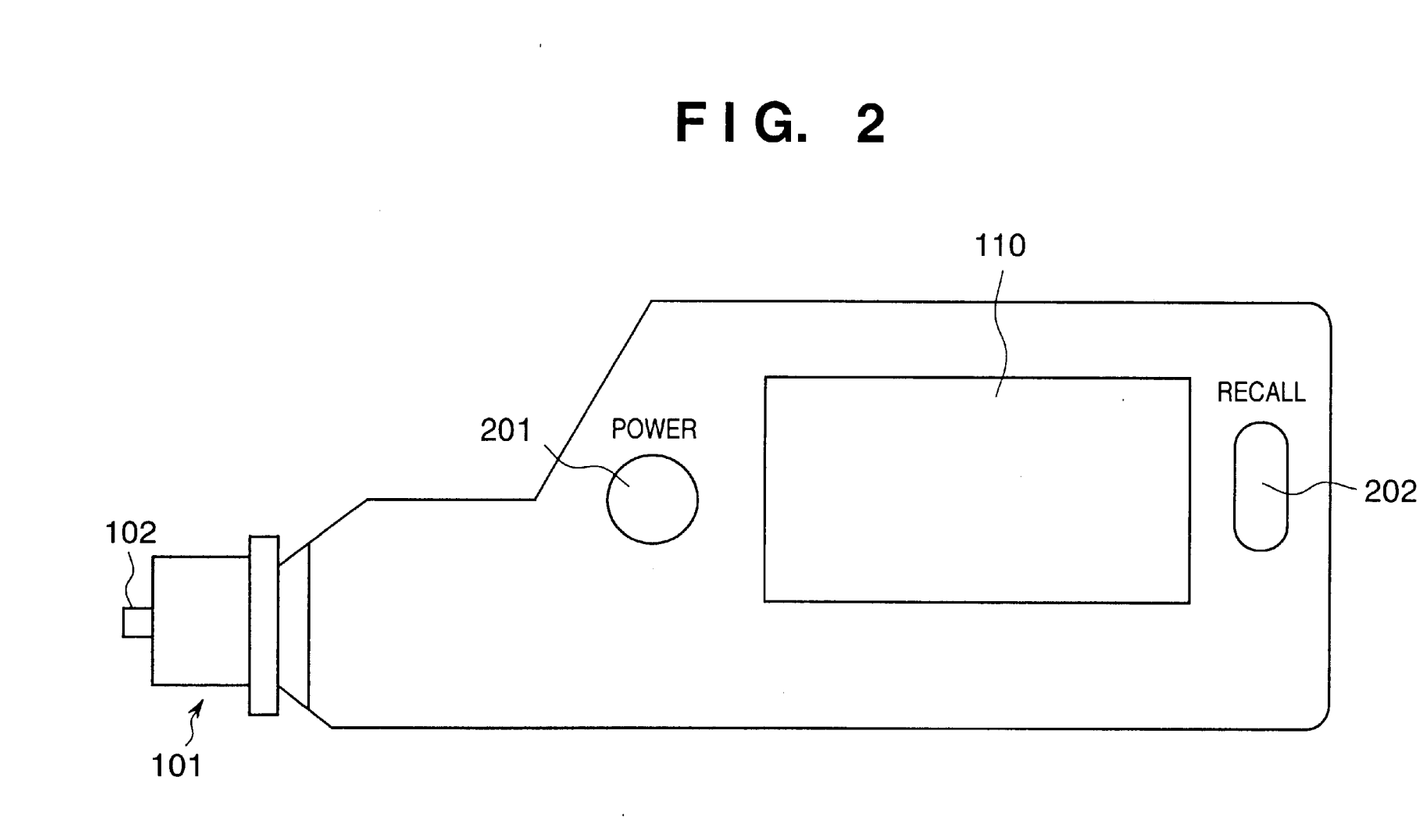
FIG. 2 is a schematic diagram showing the blood sugar measuring instrument of the embodiment of the present invention.

FIG. 1 is a block diagram schematically showing the constitution of a blood sugar measuring instrument of an embodiment of the present invention, and FIG. 2 is a schematic diagram of this blood sugar measuring instrument.

In these drawings, 101 designates a specimen (chip) which is detachably mounted on the front end of the blood sugar measuring instrument as FIG. 2 shows, and 102 designates an opening for collecting blood, which is linked to a reagent layer portion through a blood traveling portion formed of capillaries.

This reagent layer portion comprises a reagent layer 103 containing a reagent, and a blood cell filtering layer 104 for filtering blood cells. This reagent layer 103 is impregnated with a reagent required for reacting with sugar in blood and producing color, such as for example, glucose oxidase (GOD), peroxidase (POD), 4-aminoantipyrine, and N-ethyl-N-(2-hydroxy-3-sulfopropyl)-m-toluidine-sodium (TOOS). The pore diameter of the film forming the reagent layer 103 is preferably a diameter allowing blood cells to pass through, for example, 5–15 $\mu$m. By forming such a diameter, the development of blood into the reagent layer 103 is expedited, thereby speed of reaction of blood with the reagent can be increased. As the material for the film, conventionally known materials, such as nitrocellulose, can be used. The blood cell filtering layer 104 is constituted by a film having a pore diameter for filtering blood cells, for example, 0.45 $\mu$m. As the material for the film, conventionally known materials, such as polyethersulfone, can be used.

Blood enters inside the chip from the opening 102, travels through the traveling portion comprising capillaries, and reaches the reagent layer portion, where blood reacts with the reagent contained in the reagent layer 103, and is colored. Blood further travels to the blood cell filtering layer 104, where the blood cells are filtered. Reflected light is then measured from the blood cell filtering layer side.

The reagent layer portion may be constituted by one layer of film having fine pores allowing blood cell filtering and impregnated with the reagent, or may have a conventionally known multilayer structure.

A light source 105 constituting an irradiation means generates light having a predetermined wavelength, for example, 610 nm. A photo detector 106 constituting a reflected light detecting means detects the intensity of light which, after being irradiated by the light source 105, is reflected by the blood cell filtering layer 104. By this intensity of reflected light, change in color in the blood cell filtering layer 104 can be detected. An A/D converter 107 converts detection signals (analog signals) outputted from the photo detector 106 corresponding to the intensity of reflected light into digital signals.

A controller 108 controls the operation of the entire instrument, and comprises, for example, a CPU 121 such as a microprocessor, a program memory 123 for storing the control program of the CPU 121 and the like, a data memory 124 which is the RAM area for storing measured data and the like, and a temperature table 122 for storing correction data corresponding to ambient temperature (environmental temperature) sensed by a temperature sensor 127 and the like. A timer 126 measures the lapse of time as described later, and informs it to the CPU 121 by interruption or the like.

An input portion 109 comprises a key (201 in FIG. 2) for instructing the power source to be turned on or off, a key (202 in FIG. 2) for instructing the reading of measured data or the like. Numeral 110 is a display such as a liquid crystal display, and 111 is a battery for supplying electric power to the entire instrument.

Figure 3A:
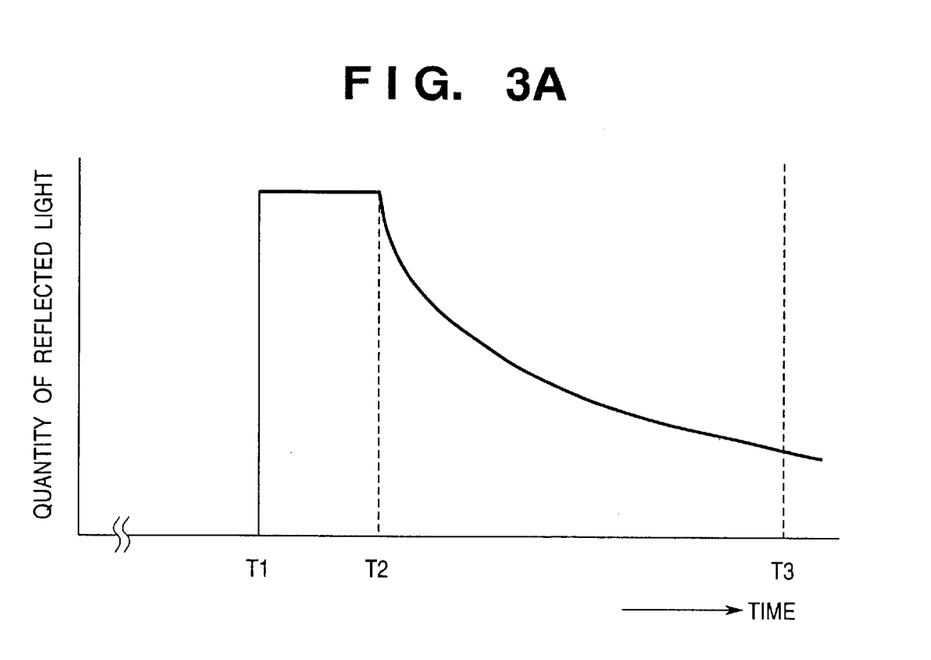
FIGS. 3A and 3B are graphs illustrating the quantity of reflected light and absorbency in the blood sugar measuring instrument of an embodiment of the present invention.
Figure 3B:
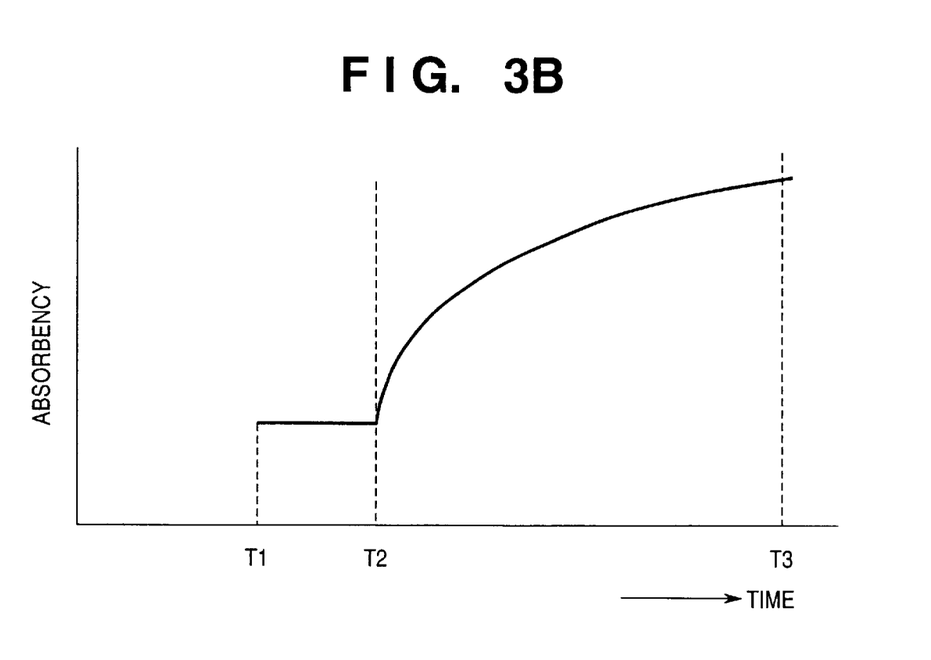

FIG. 3A is a graph showing an example of the quantity of detected reflected light; FIG. 3B is a graph showing absorbency corresponding to the intensity of the reflected light (FIG. 3A).

In FIGS. 3A and 3B, timing T1 shows the time when the chip 101 is mounted on the instrument. That is, since the reflecting surface of the blood cell filtering layer 104 of the chip 101 has a nearly or substantially white color initially (before coloration), when the chip 101 is mounted on the instrument at timing T1, the quantity of reflected light increases rapidly. In timing T1–T2, blood applied to the opening 102 travels through the traveling portion, reaches the reagent layer 103, and reacts with the reagent to produce color. Thereafter, the colored blood travels to the blood cell filtering layer 104 to color the reflecting surface, thereby the quantity of reflected light gradually begins lowering after the timing T2. When the reaction of the reagent with blood has almost completed (timing T3), the blood sugar level is calculated. The method of determining this timing T3 will be described later.

Absorbency shown in FIG. 3B is given from the quantity of reflected light before the coloration of the reagent layer takes place (Aini) and the quantity of reflected light after the coloration of the reagent layer takes place (Aaft) as:

Absorbency=(A$ini$)/(A$aft$)

The above-described measuring timing T3 is given as the time when this absorbency has reached almost equilibrium.

Figure 4:
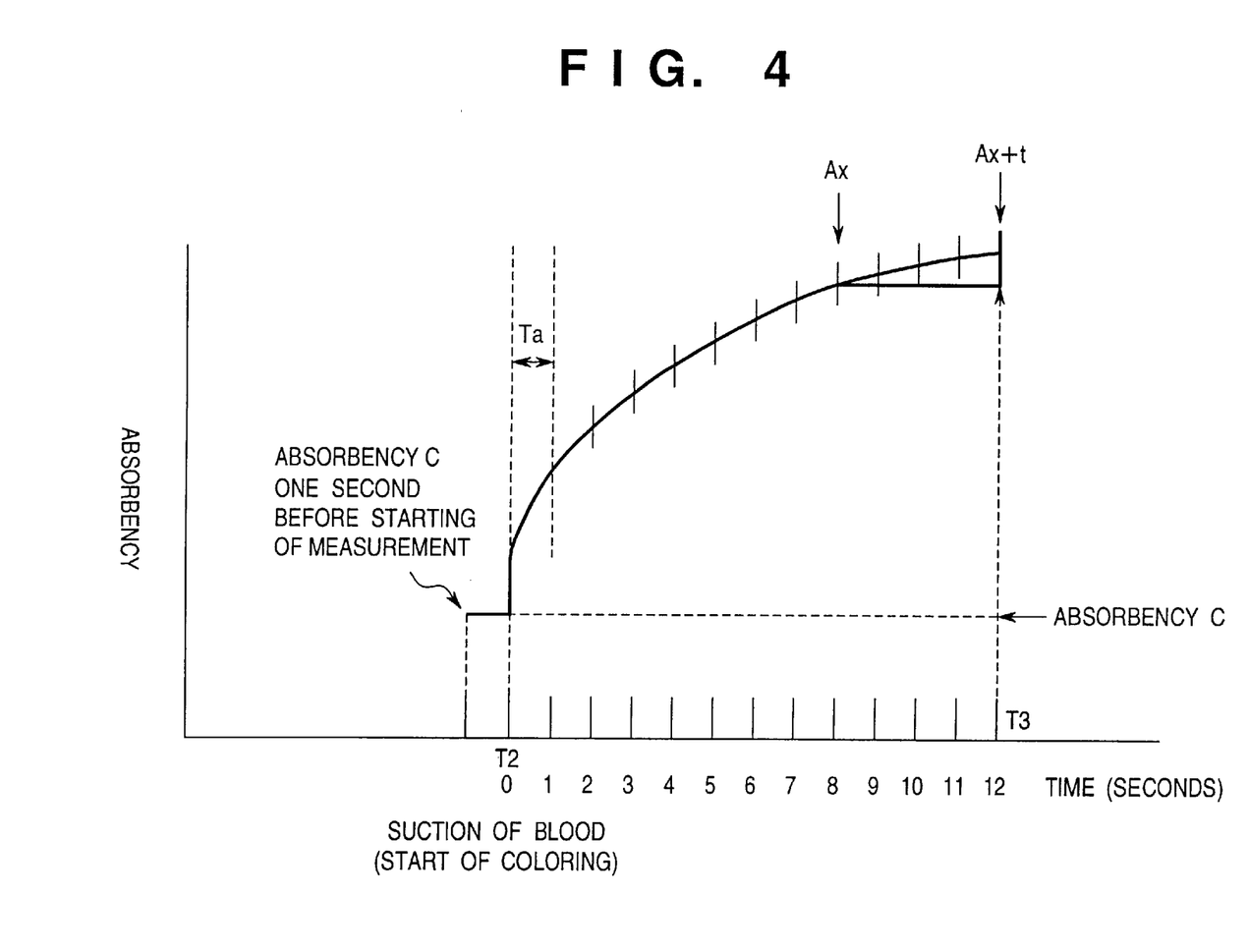
FIG. 4 is a diagram illustrating a method for determining the end point of the measurement by the blood sugar measuring instrument of the embodiment of the present invention.

FIG. 4 is a diagram illustrating how to determine the measuring timing T3 in this embodiment. Although the measuring timing T3 is shown about 12 seconds after starting the coloration of the reagent layer 104 in this example, this is of course only an example.

Absorbency one second before starting coloration at timing T2 is represented by C, and thereafter, the intensity of reflected light is measured at the time interval of Ta seconds (e.g. 1 second) to calculate absorbency. If absorbency X seconds after starting measurement is represented by Ax, and absorbency (X+t) seconds after starting measurement is represented by Ax+t(X≧t: e.g. t=4 sec):

$\Delta Ax = Ax - C$ $\Delta Ax+t = Ax+t - C$ $(\Delta Ax+t - \Delta Ax)/t = \Delta D$(change in absorbency per second: averaged value in $t$ seconds)

$(\Delta D/\Delta Ax+t) \times 100 \leq d(\%)(d=2(\%))$

That is, on the basis of absorbency X seconds after starting measurement, Ax, and absorbency (X+t) seconds after starting measurement, Ax+t, the reaction of the reagent with the blood is considered to have almost completed when change in absorbency per second, ΔD, has become d (2%) or less, and the blood sugar level is determined on the basis of absorbency at that time.

In the described embodiment, t is more than two seconds, preferably 2–6 seconds. As described above, t is more than 2 seconds and a changing rate of the measured values for every one second is obtained based on an average value of measured values for t seconds such that an error occurring at one second can be absorbed.

Figure 5:
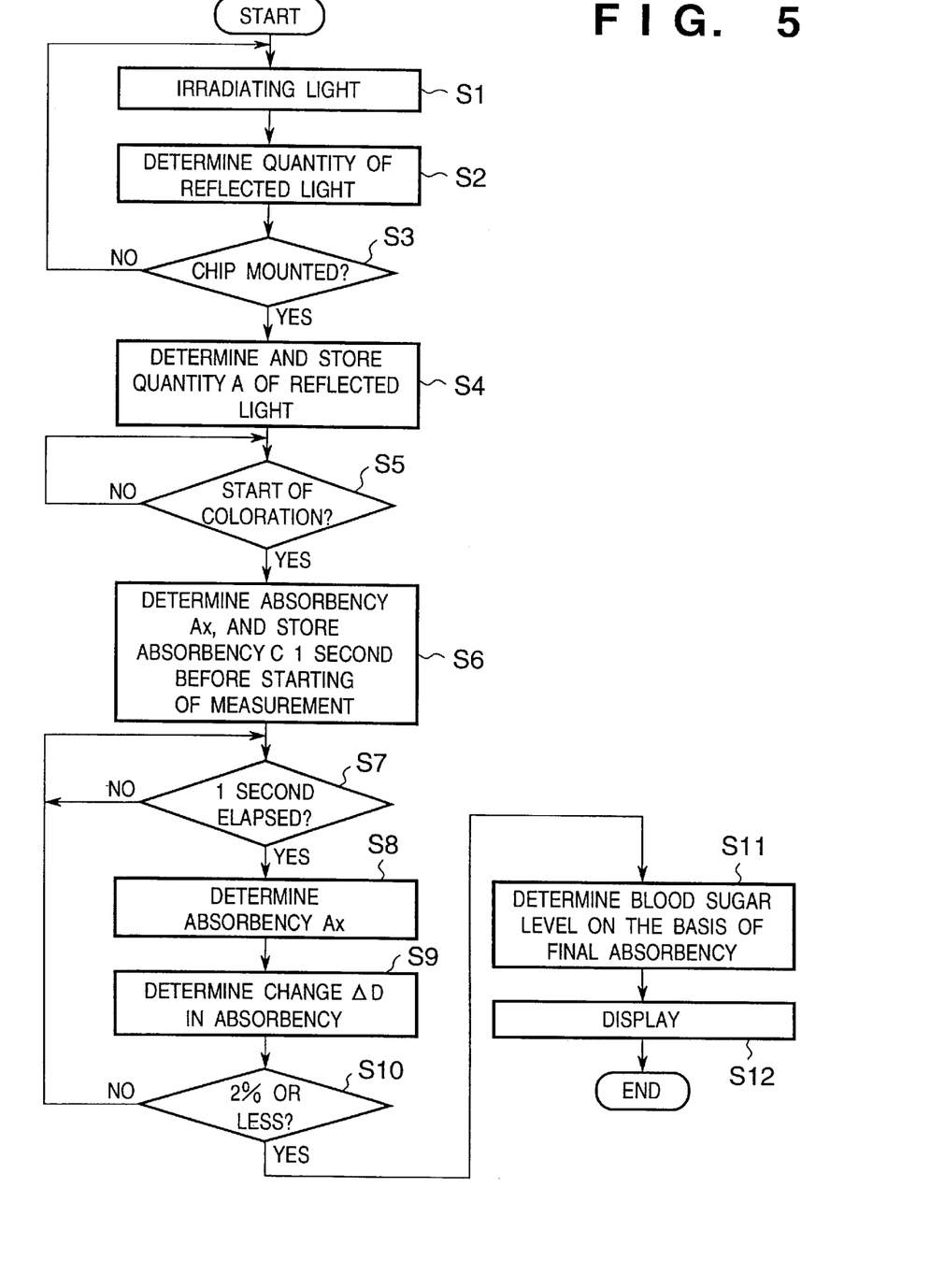
FIG. 5 is a flowchart showing the process of measurement by the blood sugar measuring instrument of the embodiment of the present invention.

FIG. 5 is a flowchart showing the process of measurement in the blood sugar measuring instrument of this embodiment. The control program for implementing this process is stored in the program memory 123 of the above-described controller 108.

First, in step S1, the light source 105 is made to emit light intermittently, and in step S2, the intensity of reflected light detected by the photo detector 106 is read. Whether the chip 101 is mounted or not is detected on the basis of the intensity of the reflected light (step S3), and when the intensity of the reflected light increases as shown in the timing T1 of FIG. 3A, it is judged that the chip 101 has been mounted.

The process thus proceeds from step S3 to step S4, when the quantity of reflected light A is obtained and stored in the data memory 124. Next, in step S5, whether the reagent layer 104 has started coloration or not is checked. When the coloration of the reagent layer 104 has started and the quantity of reflected light has started lowering, the process proceeds to step S6, and the time is judged to be the timing T2 for starting measurement. Absorbency one second before T2, C, is obtained and stored in the data memory 124 with the intensity of the reflected light at that time, and absorbency Ax is determined on the basis of the intensity of reflected light at the start of the measurement. Thus, the process is proceeded to the measurement of blood sugar shown by timings T2 to T3 in FIGS. 3A and 3B.

In this measurement, first in step S7, elapsing one second is waited on the basis of time measurement with the timer 126, and when one second is elapsed, the process proceeds to step S8 to obtain absorbency Ax on the basis of the intensity of the reflected light at that time. The process is then proceeded to step S9, where whether absorbency t seconds before, Ax-t, is stored or not is checked, if stored, then the difference (Ax−Ax-t) is obtained, and change in absorbency per second (ΔD) is determined from the averaged value. This thus forms a calculation means that calculates an average value of the intensity per second based on intensities detected by the photo detector 106. The process proceeds to step S10 which forms a determination means that determines whether the value of the change (ΔD) is 2% or less, and if not, the process is returned to step S7 and the above-described process is repeated. In first 4 seconds from the start of measurement, since no data on previous absorbency are present, the process of step S9 is practically skipped.

Thus, from step S10, the process proceeds to step S11 when change in absorbency per second becomes a first predetermined value or less, namely 2% or less. Based on the absorbency at that time, the concentration of glucose contained in the blood applied to the chip 101 is calculated to determine the blood sugar level of the subject, thus constituting a blood sugar calculating means. The result is indicated on the display 110. The formula for calculating the concentration of glucose X is represented, for example, when the absorbency at the time of measurement is K, as follows:

$$X = a0 + a1 \cdot K + a2 \cdot K^2 + a3 \cdot K^3$$

where a0, a1, a2, and a3 are constants.

The value d for determining time intervals for measurement Ta and t, and timing for measurement T3 in the above-described embodiment is not limited to the above values, but it is of course possible to store the relationship between absorbency experimentally obtained and the concentration of glucose as a table, and to determine the corresponding blood sugar level from finally obtained absorbency.

In this embodiment, since the speed of reaction of the reagent in the reagent layer 103 varies depending on environmental temperatures, the measured absorbency or the finally determined blood sugar level is corrected referring to the temperature table 122 on the basis of the temperature value measured by the temperature sensor 127.

According to this embodiment, it is not required to always wait a predetermined time until the result of measurement is obtained, and since the measurement is performed at the most effective timing (the time when the reaction of the reagent has almost completed), accurate results of measurement can be obtained.

Figure 6:
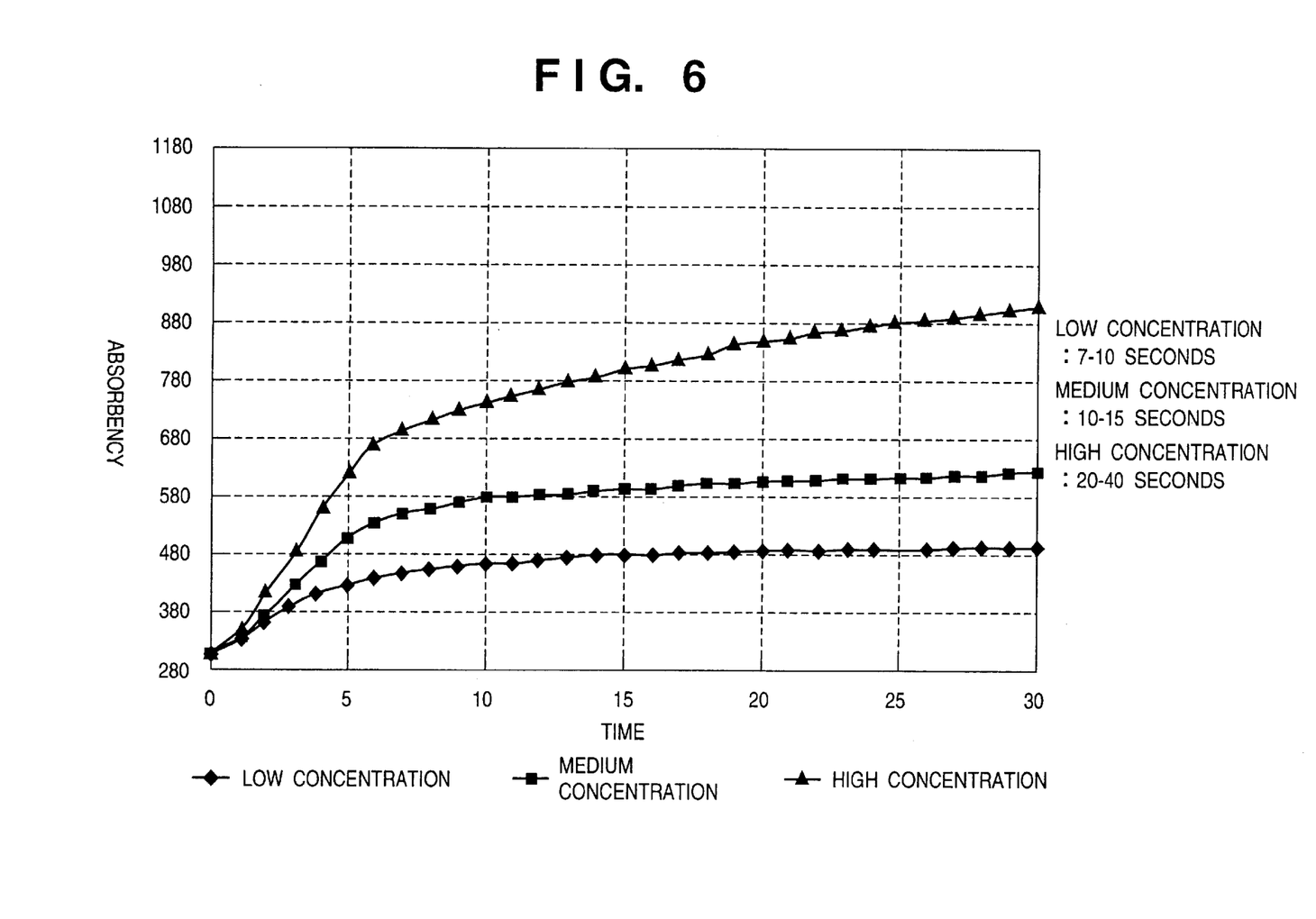
FIG. 6 is a diagram illustrating change in absorbency by blood sugar levels.
Figure 7:
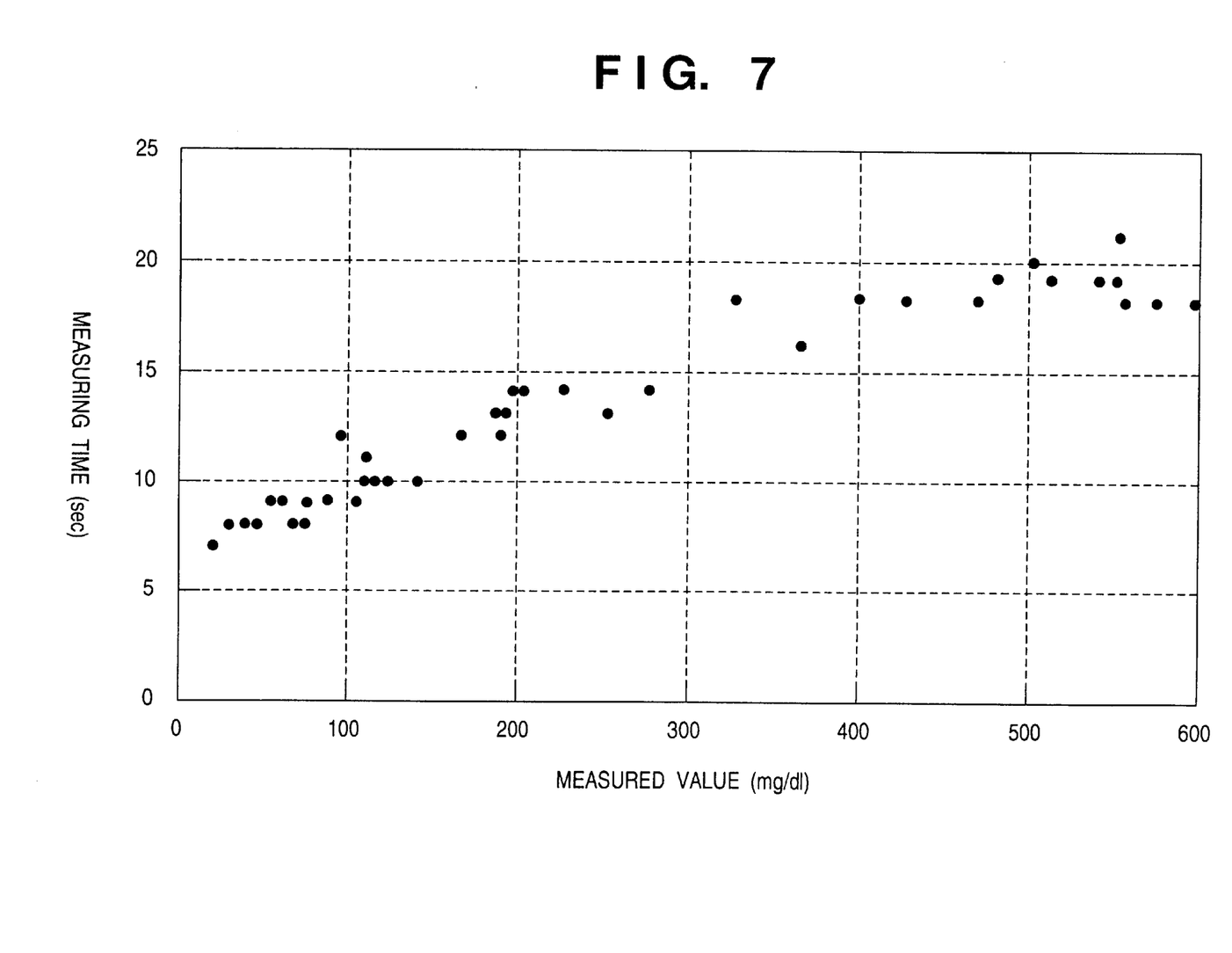
FIG. 7 is a diagram showing relationship between blood sugar levels and measuring time.

FIG. 6 is a graph showing the relationship between the concentration of glucose in blood and absorbency and FIG. 7 is a graph showing the relationship between the concentration of glucose in blood and the length of time required for measurement.

As apparent from these graphs, it is known that the time until the absorbency almost reaches equilibrium increases with increase in the concentration of glucose. That is, time required for measurement decreases for blood having a low glucose concentration, and the time increases with increase in the concentration. Therefore, for example, an accurate blood sugar level can be measured even if the concentration of glucose is high.

[Embodiment 2]

Next, Embodiment 2 of the present invention will be described. In this Embodiment 2, an instrument and method for displaying the state of measurement-especially effective when the length of time until measurement is completed is not constant as above-described Embodiment 1.

Figure 8:
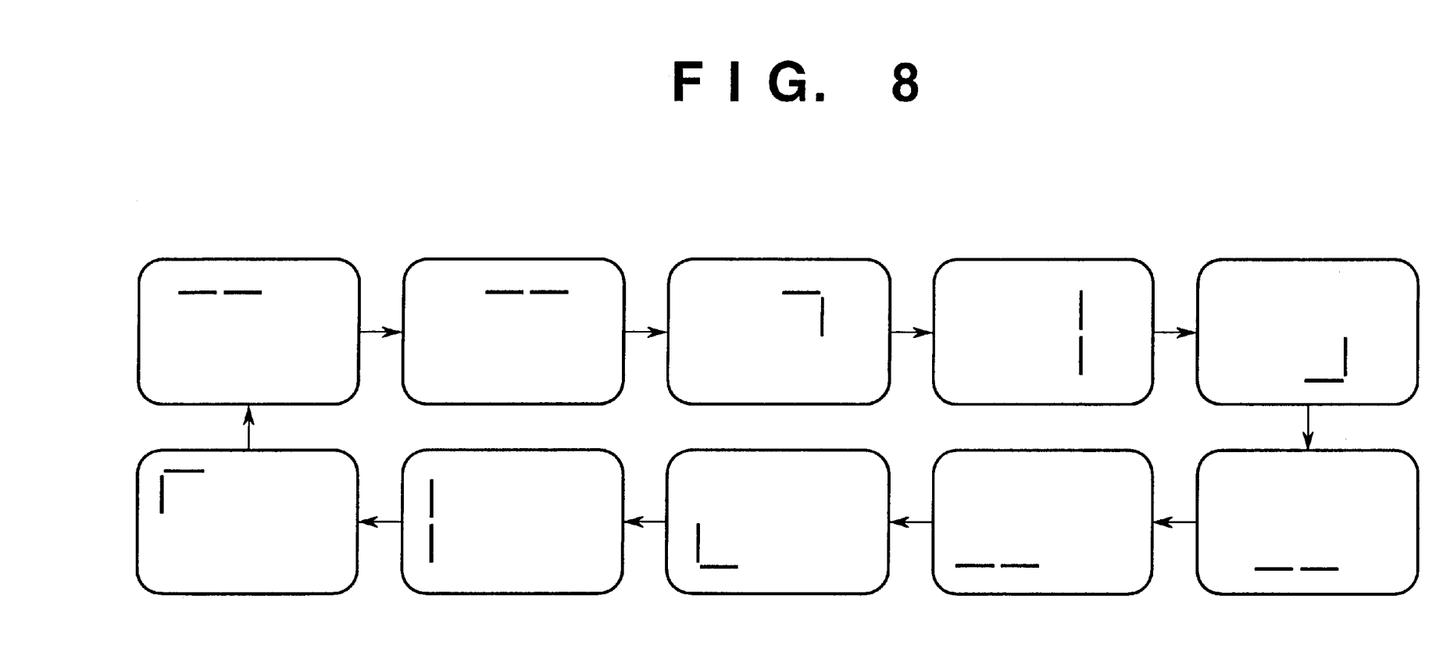
FIG. 8 is a diagram showing the display mode in a blood sugar measuring instrument of the second embodiment of the present invention.

In this Embodiment 2, rotating and moving marks (predetermined marks), for example, as shown in FIG. 8 are displayed on the display 110 (roulette display), and the speed of rotating and moving is changed corresponding to the remaining time until the completion of measurement. In FIG. 8, the modes of displaying change in the direction are shown by arrows. This thus constitutes a notifying means providing notification that the blood sugar level is being measured.

Figure 9:
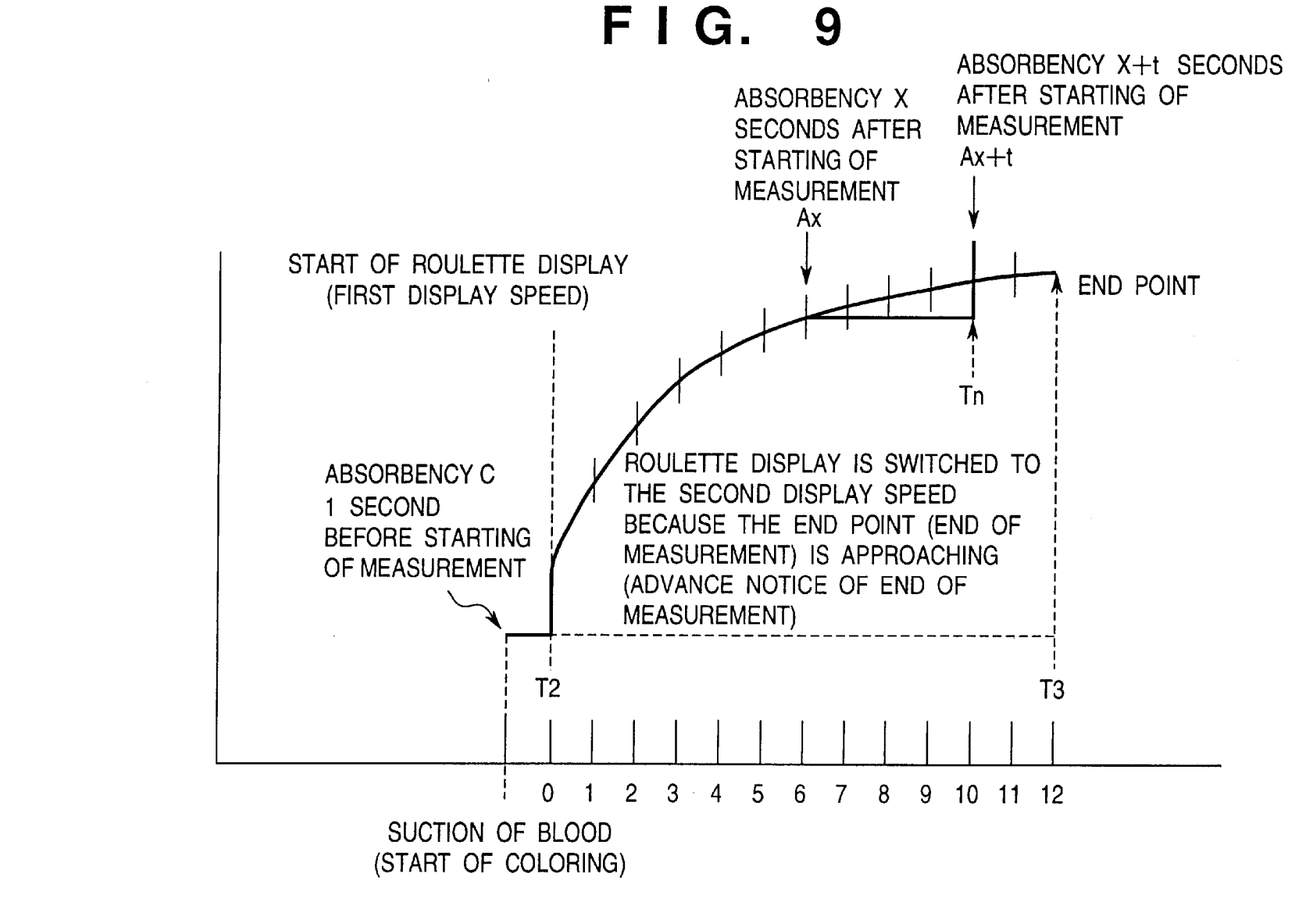
FIG. 9 is a diagram illustrating a method for determining the end point of the measurement by the blood sugar measuring instrument of the second embodiment of the present invention.

FIG. 9 is a diagram illustrating such a method of displaying, and corresponds to the above-described FIG. 4.

As in case of FIG. 4, absorbency when coloration begins at timing T2 is represented by C, and thereafter, the intensity of reflected light is measured at the time interval of Ta seconds (e.g. 1 second) to calculate absorbency. At the same time, at timing T2, marks, for example shown in FIG. 8, are displayed, and the modes of displaying are shifted in the direction of arrows in FIG. 8, for example, each time one second is elapsed (the first display mode).

If absorbency X seconds after starting measurement is represented by Ax, and absorbency (X+t) seconds after starting measurement is represented by Ax+t(X≧t: e.g. t=4 sec):

$$\Delta Ax = Ax - C$$

$$\Delta Ax+t = Ax+t - C$$

$(\Delta Ax+t-\Delta Ax)/t=\Delta D$(change in absorbency per second: averaged value in $t$ seconds)

$(\Delta D/\Delta Ax+t)\times 100 \leq d1(\%)(d1=5(\%))$

That is, on the basis of absorbency X seconds after starting measurement, Ax, and absorbency (X+t) seconds after starting measurement, Ax+t, the moving speed of the marks displayed on the display 110 is changed when the change in absorbency per second, ΔD, has become d (5%) or less (the second display mode: e.g. about every two or more seconds) to inform the user or the subject that the completion of measurement is approached. This change in absorbency per second of 5% constitutes a second predetermined value.

Finally, when change in absorbency per second has become 2% or less, it is judged that the reaction of the reagent with the blood has almost completed, and the blood sugar level is determined on the basis of absorbency at that time.

Figure 10:
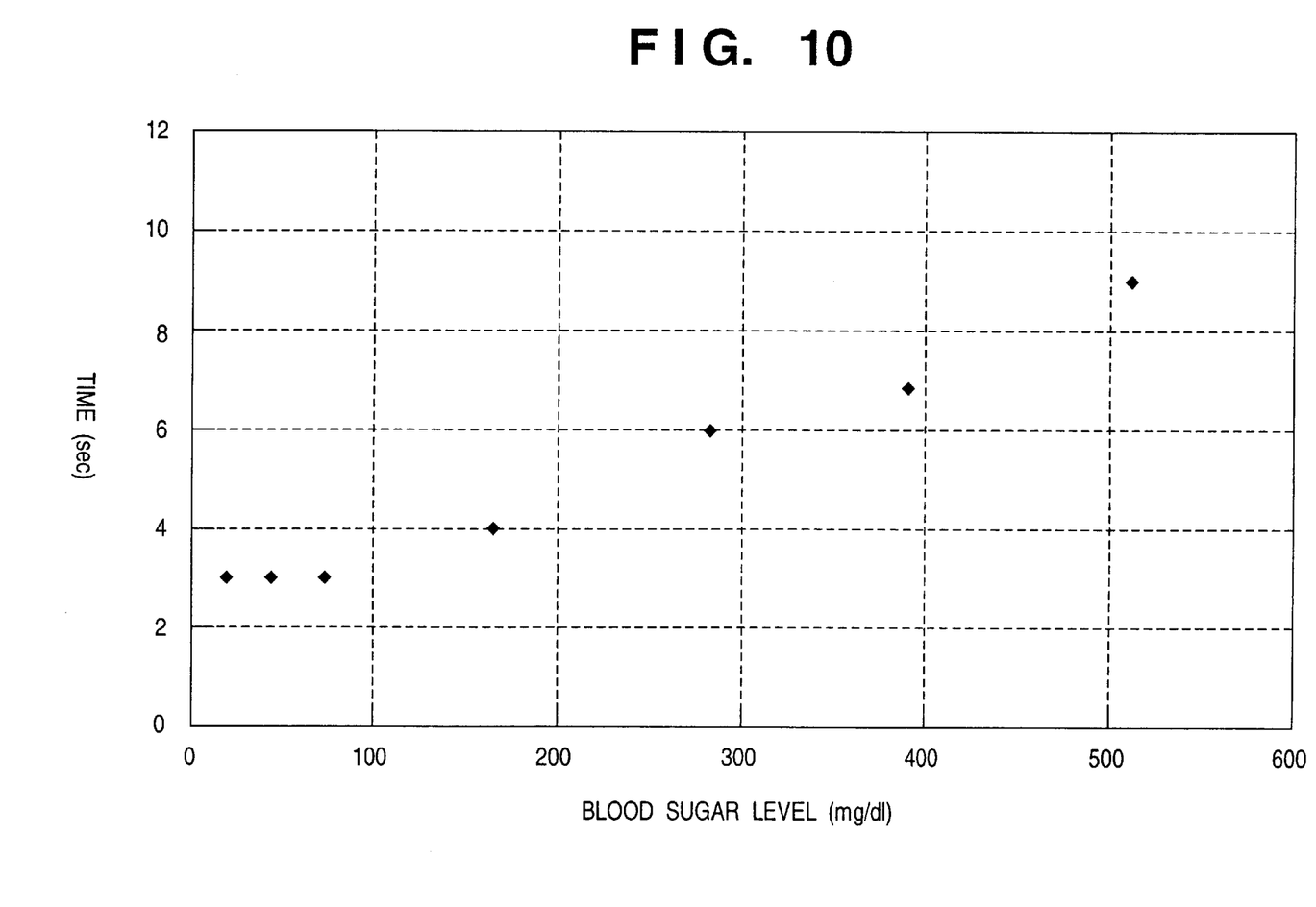
FIG. 10 is a diagram showing time since the display mode has been. changed until the end of measurement corresponding to blood sugar levels in the second embodiment of the present invention.

FIG. 10 is a diagram showing time T from the time when the display is shifted to the above-described second mode to the time when the measurement is completed corresponding to blood sugar levels (glucose concentrations).

In this diagram also, it is known that the length of time required for measurement increases with increase in blood sugar levels. For example, when the glucose concentration is low, the above-described time T is about 3 seconds; when the concentration is medium, T is about 3 to 6 seconds; and when the concentration is high, T is about 6 to 9 seconds.

Figure 11:
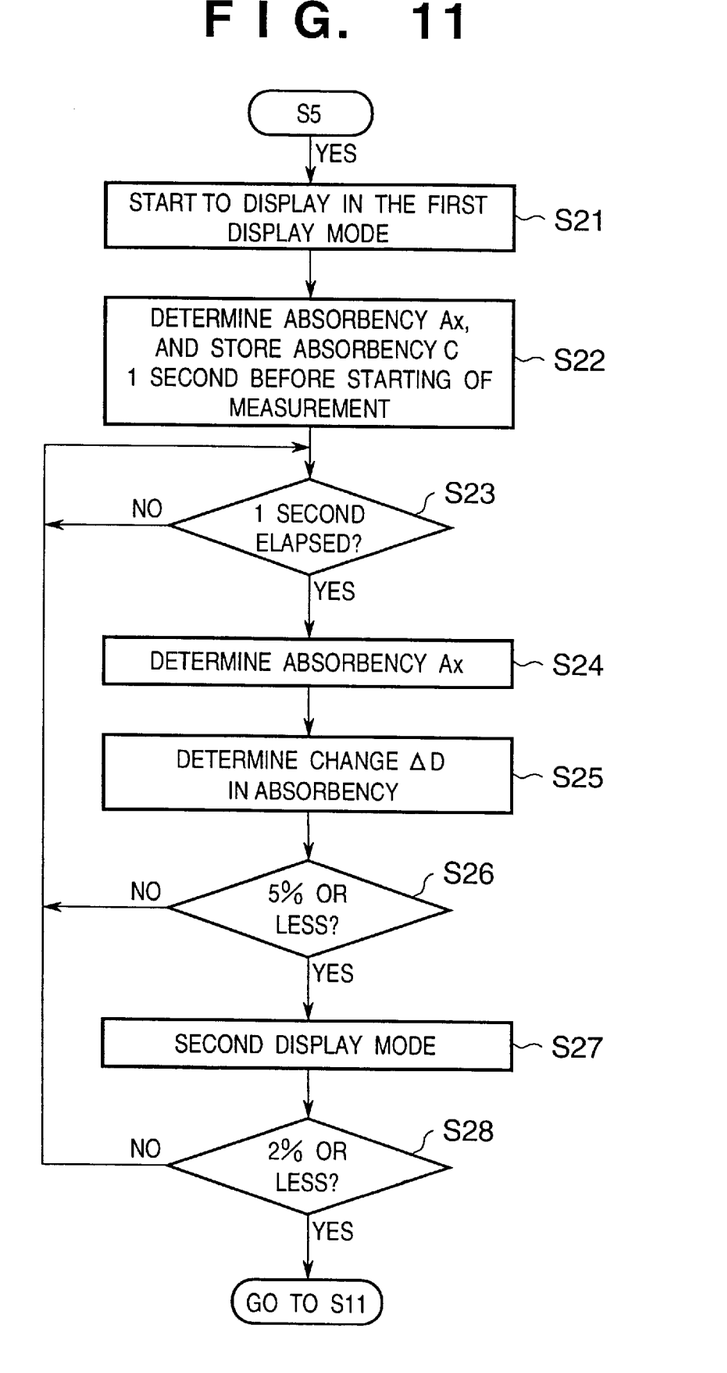
FIG. 11 is a flowchart showing the process of measurement by the blood sugar measuring instrument of the second embodiment of the present invention.

FIG. 11 is a flowchart showing the process of measurement in this Embodiment 2, from which description of the portions same as those of the above-described FIG. 5 are omitted.

Here, when the coloration of the blood cell filtering layer 104 in the above-described FIG. 5 begins, the process is proceeded to step S21, and display in the first display mode is started. Then, the process is proceeded to step S22, the time is judged as the timing for starting measurement, T2, and absorbency one second-before T2, C, is determined and stored in the data memory 124 with the intensity of the reflected light at that time, and absorbency Ax is determined on the basis of the intensity of reflected light at that time. Then, the process is proceeded to blood sugar measuring process shown by timings T2 and T3 in FIG. 9.

In this measurement, first in step S23, elapsing one second is waited on the basis of time measurement with the timer 126, and when one second is elapsed, the process is proceeded to step S24 to obtain absorbency Ax on the basis of the intensity of the reflected light at that time. The process is then proceeded to step S25, where whether absorbency t seconds before, Ax-t, is stored or not is checked, if stored, then the difference (Ax−Ax-t) is obtained, and change in absorbency per second (ΔD) is determined from the averaged value. The process is proceeded to step S26, where whether the value of the change (ΔD) is 5% or less is checked, and if not, the process is returned to step S23 and the above-described process is repeated. In first 4 seconds from the start of the measurement, since no data on previous absorbency are present, the process of the step S25 is practically skipped. When change per second has become 5% or less, the process is proceeded to step S27, and the display mode is shifted to the second display mode in which the moving speed of the above-described marks is changed (e.g. lowered). A notifying control means is thus provided which controls and changes the mode of notification performed by the notifying means. Furthermore, in the next step S27, whether the value of change ΔD is 2% or less is checked, and if not, the process is returned to step S23, but when change per second has become 2% or less, the process is proceeded to step S11 in FIG. 5 described above, and on the basis of absorbency at that time, the concentration of glucose contained in the blood applied to the chip 101 is calculated to determine the blood sugar level of the subject. The result is indicated on the display 110.

The above-described first and second display modes are not limited to the display of this embodiment, but may be displays such as digital displays or clocks.

When the mode of displaying is changed from the first display mode to the second display mode, it is preferable that the length of time from shifting to the second display mode to the completion of measurement is substantially constant, because the user can estimate the length of time until the completion of measurement. In this case, since the time taken for measurement differs depending on the blood sugar level as described above, timing for shifting from the first display mode to the second display mode is changed depending on absorbency.

That is, as the above-described FIG. 6 shows, when absorbency is a certain value (e.g. 600) or more, the condition to shift to the second display mode in the above-described FIG. 9 (change per second ΔD: 3%) is established. By this, in the case of high concentration, timing to shift to the second display mode is delayed, and even if the time until the completion of measurement increases due to a high blood sugar level, the length of time after shifting to the second display mode to the completion of measurement can be substantially constant.

Also in the above-described Embodiments 1 and 2, the temperature table 122 stores correction information at, for example, 10° C., 15° C., 20° C., and 30° C., and on the basis of this correction information, the obtained blood sugar levels are corrected.

Figure 12:
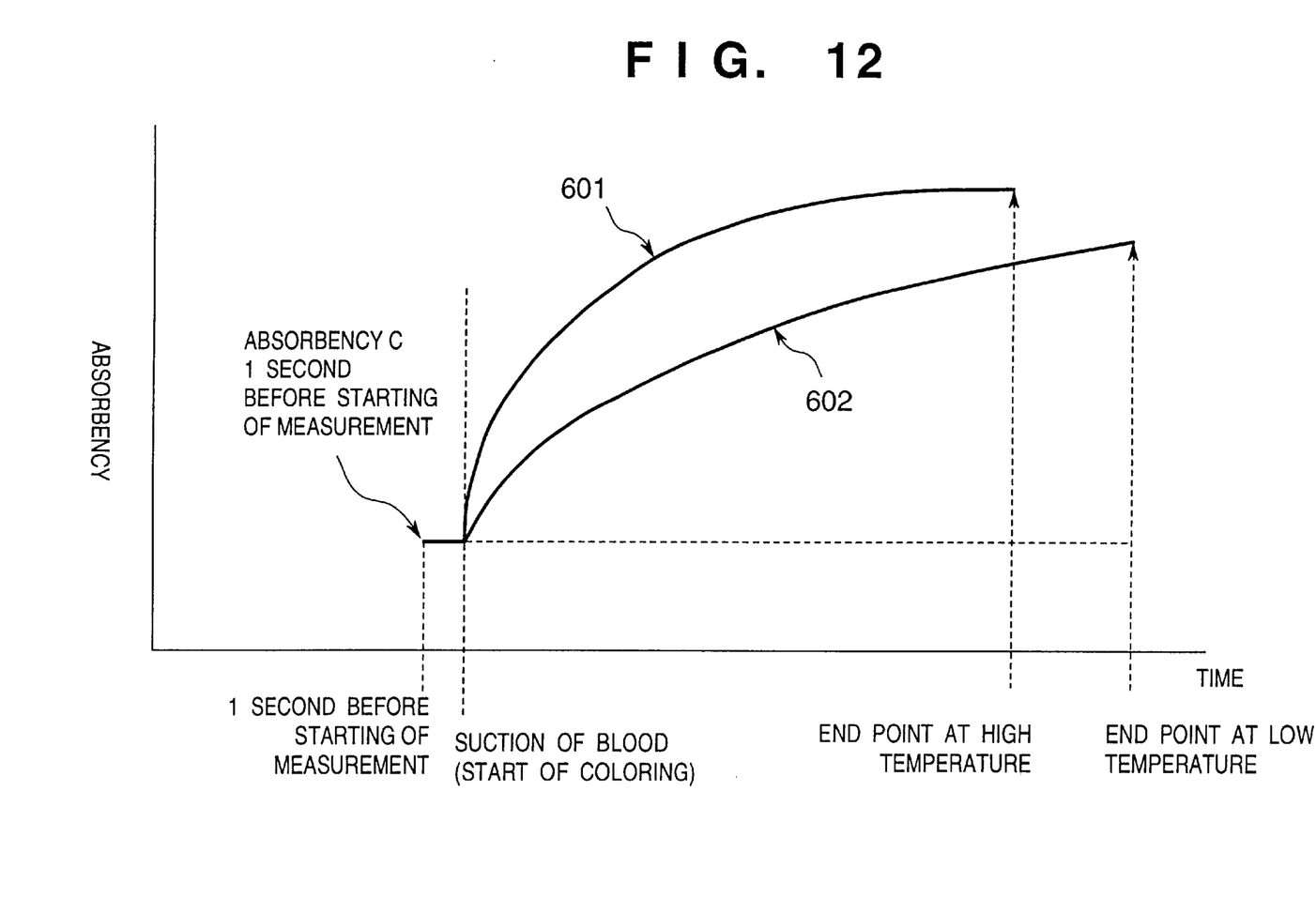
FIG. 12 is a diagram showing change in absorbency of the same blood due to ambient temperatures.
Figure 13:
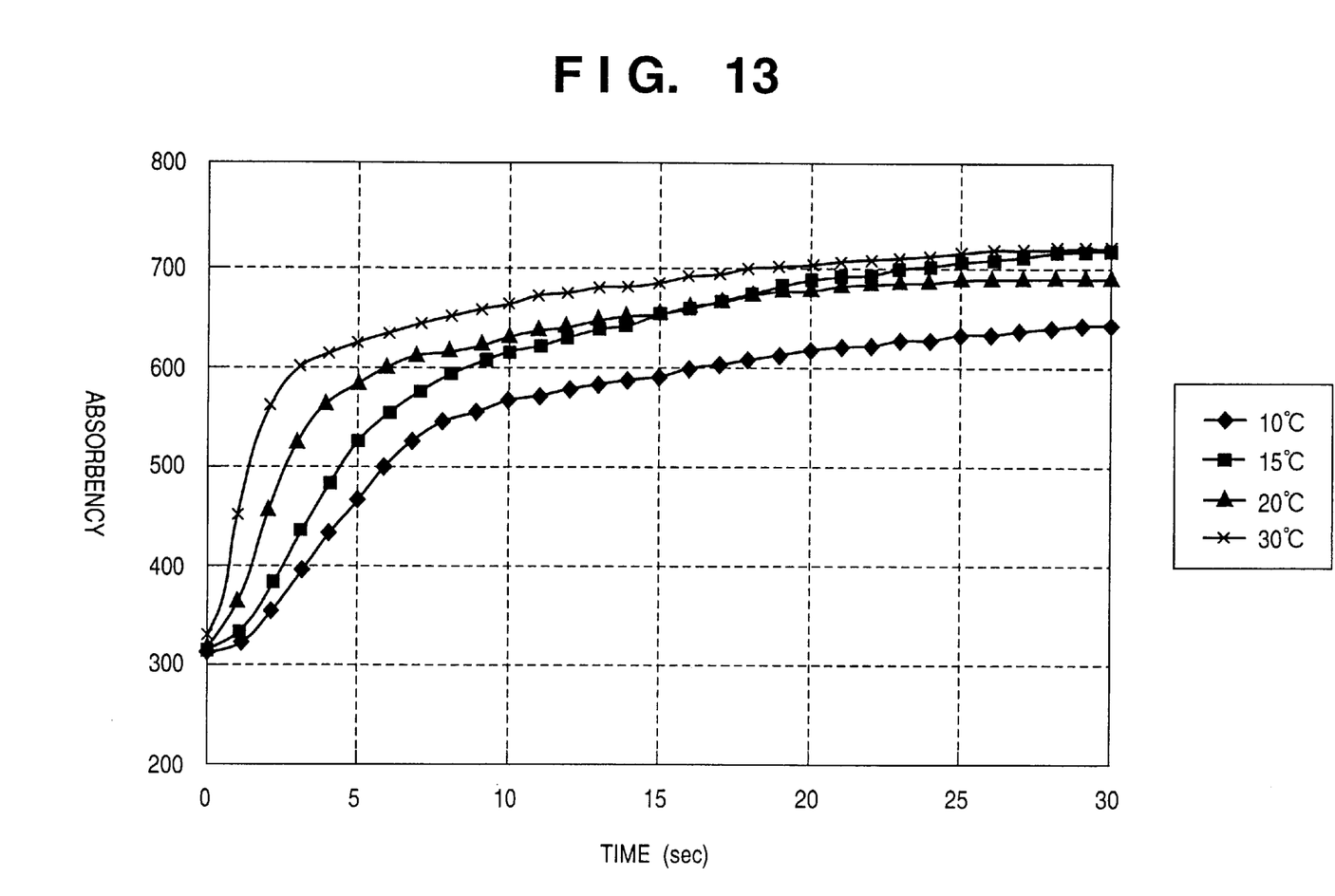
FIG. 13 is a graph showing change in absorbency due to temperatures.

FIG. 12 is a diagram showing change in absorbency of the same blood depending on ambient temperatures, and FIG. 13 is a graph showing difference in absorbency due to temperatures.

In FIG. 12, numeral 601 denotes change in absorbency when ambient temperature is high, and 602 denotes change in absorbency when ambient temperature is low. Thus, the coloration of the reagent is delayed as ambient temperature lowers, the time until the end point is reached becomes long, and the absorbency at the completion of measurement is also lowered. On the contrary, as ambient temperature increases, the coloration of the reagent becomes quick, the time until the end point is reached becomes short, and the absorbency at the completion of measurement is also increased.

Therefore, in the blood sugar measuring instrument of this embodiment, in order to correct such a measurement error of the blood sugar level due to ambient temperature, a temperature sensor 127 is provided for sensing ambient temperature, and conversion from the absorbency to the blood sugar level for obtaining the blood sugar level from the absorbency is corrected.

As described above, according to this embodiment, display can be performed at most adequate timing.

Also, according to this embodiment, since the state of measurement can be informed to the user, there is the effect of ease of using.

Also, the situation in which the user must unnecessarily wait until the completion of measurement can be prevented.

Also, the occurrence of measurement error due to temperature can be prevented.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims be embraced thereby.

What is claimed is:

1. A blood sugar measuring instrument for measuring blood sugar level of blood impregnated in a reagent layer of a specimen, said instrument comprising:

irradiation means for irradiating light towards the reagent layer;

reflected light detecting means for detecting an intensity of the light reflected from the reagent layer;

calculation means for calculating a change of the intensity per each second, based on the intensity detected by the reflected light detecting means over a plurality of seconds;

determination means for determining whether or not the change of the intensity calculated by the calculating means has become a first predetermined value or less; and blood sugar calculating means for calculating the blood sugar level of said blood on the basis of the intensity of the light reflected from the reagent layer when the determination means determines that the change has become the first predetermined value or less.

2. The blood sugar measuring instrument according to claim 1, wherein said determination means detects whether or not the change of the intensity has become a first predetermined value or less on the basis of absorbency obtained from the intensity of the reflected light from said specimen before reacting with said blood, and the intensity of the reflected light after said specimen has been colored by the reaction with said blood.

3. The blood sugar measuring instrument according to claim 1, further comprising:

notifying means for notifying that the blood sugar level is measuring; and notifying control means for controlling a mode of notification of said notifying means to change the mode when the change of the intensity becomes larger than said first predetermined value, and becomes a second predetermined value which is present before said first predetermined value.

4. The blood sugar measuring instrument according to claim 3, wherein said notifying control means further notifies that measurement is started when coloration of said specimen is detected.

5. The blood sugar measuring instrument according to claim 1, wherein said specimen has:

an opening for applying blood, a traveling portion to which blood applied to said opening travels, and a reagent layer portion colored by the reaction with blood having passed through said traveling area, and that said reflected light detecting means detects reflected light from said reagent layer portion.

6. The blood sugar measuring instrument according to claim 5, wherein said reagent layer portion comprises a reagent layer which is colored by the reaction with blood, and a filter layer for filtering blood cells of the blood.

7. The blood sugar measuring instrument according to claim 5, wherein an initial color of said reagent layer portion is substantially white.

8. The blood sugar measuring instrument according to claim 3, wherein said notifying means moves and displays a predetermined mark at a predetermined speed, and said notifying control means changes a speed of movement of said predetermined mark when said second predetermined quantity is reached.

9. A method for measuring blood sugar level of blood impregnated to a reagent layer of a specimen comprising:

directing light toward the reagent layer;

detecting an intensity of light reflected from the reagent layer;

calculating a change of the intensity each second based on the intensities detected over a plurality of seconds;

determining whether the change has reached a first predetermined value or less;

calculating the blood sugar level of the blood based on the intensity of light reflected from the reagent layer when the change has reached the first predetermined value or less.

10. The method for measuring the blood sugar level of blood according to claim 9, wherein the change is determined based on absorbency obtained from the intensity of the light reflected from the specimen before reacting with the blood and the intensity of the light reflected from the specimen after the specimen has been colored by the reaction with the blood.

11. The method for measuring the blood sugar level of blood according to claim 9, further comprising:

providing notification by way of a notification mode that the blood sugar level is being measured; and changing the notification mode when the change becomes larger than said first predetermined value and has reached a second predetermined value which is present before the first predetermined value.

12. The method for measuring the blood sugar level of blood according to claim 11, wherein the notification includes providing notification that measurement of the blood sugar is started when coloration of the specimen is detected.

13. The method for measuring the blood sugar level of blood according to claim 9, wherein the specimen includes an opening for applying blood, a traveling area to which travels blood applied to the opening, and a reagent layer portion colored by reaction with blood that has passed through the traveling area, the method including detecting light reflected from the reagent layer portion.

14. The method for measuring the blood sugar level of blood according to claim 13, wherein the reagent layer portion comprises a reagent layer which is colored by reaction with the blood, and a filter layer for filtering blood cells of the blood.

15. The method for measuring the blood sugar level of blood according to claim 13, wherein an initial color of the reagent layer portion is substantially white.

16. The method for measuring the blood sugar level of blood according to claim 11, wherein the notification includes moving a predetermined mark at a predetermined speed and displaying the predetermined mark, and the changing of the notification mode including changing the speed of movement of the predetermined mark when the second predetermined quantity is reached.

17. The method for measuring the blood sugar level of blood according to claim 11, wherein the changing of the notification mode includes changing the second predetermined quantity corresponding to a measured glucose concentration.

18. The method for measuring the blood sugar level of blood according to claim 9, including measuring ambient temperature and determining the blood sugar level based in the measured ambient temperature.

19. The blood sugar measuring instrument according to claim 1, wherein the plurality of seconds is two seconds to six seconds.

20. The method for measuring the blood sugar level of blood according to claim 9, wherein the calculation of the change of the intensity per each second is based on the intensities detected between two seconds to six seconds.

* * * * *